(12) United States Patent
Vanderbroucke et al.

(10) Patent No.: US 9,713,910 B2
(45) Date of Patent: Jul. 25, 2017

(54) TABLETTING SYSTEM

(71) Applicant: GEA Process Engineering nv, Halle (BE)

(72) Inventors: Freddy Gerard Luc Vanderbroucke, Roux (BE); Jan Vogeleer, Bornem (BE); Michel Simon Waldron, Southampton (GB)

(73) Assignee: GEA PROCESS ENGINEERING NV (BE)

( * ) Notice: Subject to any disclaimer, the term of this patent is extended or adjusted under 35 U.S.C. 154(b) by 0 days.

(21) Appl. No.: 14/901,141

(22) PCT Filed: Jun. 27, 2013

(86) PCT No.: PCT/IB2013/055284
§ 371 (c)(1),
(2) Date: Dec. 28, 2015

(87) PCT Pub. No.: WO2014/207510
PCT Pub. Date: Dec. 31, 2014

(65) Prior Publication Data
US 2016/0243781 A1 Aug. 25, 2016

(51) Int. Cl.
*B30B 15/30* (2006.01)
*B30B 11/08* (2006.01)
*A61K 9/20* (2006.01)

(52) U.S. Cl.
CPC .......... *B30B 15/302* (2013.01); *A61K 9/2095* (2013.01); *B30B 11/08* (2013.01)

(58) Field of Classification Search
None
See application file for complete search history.

(56) References Cited

U.S. PATENT DOCUMENTS

| 2011/0037185 A1 | 2/2011 | Kowalski et al. | |
| 2012/0061869 A1* | 3/2012 | Boeckx | A61J 3/10 264/40.1 |
| 2014/0234463 A1 | 8/2014 | Ozeki et al. | |

FOREIGN PATENT DOCUMENTS

| CA | 2851206 A1 | 4/2013 |
| CN | 201 264 384 Y | 7/2009 |
| CN | 202 702 665 U | 1/2013 |
| DE | 44 37 823 A1 | 4/1996 |
| EP | 275834 A1 | 7/1988 |
| EP | 0299065 A1 | 1/1989 |
| EP | 2151401 A1 | 2/2010 |
| EP | 2 384 746 A2 | 11/2011 |
| EP | 2764989 A1 | 8/2014 |
| JP | 51-022467 B | 7/1976 |
| JP | 61-133131 A | 6/1986 |
| JP | S63 5900 A | 1/1988 |
| JP | 63-174657 A | 7/1988 |

(Continued)

*Primary Examiner* — Mary F Theisen
(74) *Attorney, Agent, or Firm* — Condo Roccia Koptiw LLP

(57) ABSTRACT

The tabletting system (1) comprises a rotary tablet press (6) with a tablet press feeder (67). A first material feeder (21) and a second material feeder (22) are connected to a blender (4) with an inlet end (40) and a discharge end (45). The discharge end (45) of the blender is in close connection with the tablet press. The inlet end (40) of the blender (4) is positioned at a level (u) higher than the level (v) of the discharge end (45) in the vertical direction.

18 Claims, 3 Drawing Sheets

(56) References Cited

FOREIGN PATENT DOCUMENTS

| | | |
|---|---|---|
| JP | H09 271996 A | 10/1997 |
| JP | 2011-131381 A | 7/2011 |
| JP | 2012-525895 A | 10/2012 |
| JP | 2013-060503 A | 4/2013 |
| WO | WO 02/067854 A2 | 9/2002 |
| WO | WO 03/020499 A1 | 3/2003 |
| WO | WO 2010/128359 A1 | 11/2010 |
| WO | WO 2013/051262 A1 | 4/2013 |
| WO | WO 2013051262 A1 | 4/2013 |

* cited by examiner

TABLETTING SYSTEM

CROSS REFERENCE TO RELATED APPLICATIONS

This application is the National Stage Entry under 35 U.S.C. §371 of Patent Cooperation Treaty Application No. PCT/IB2013/055284, filed Jun. 27, 2013 the contents of which are hereby incorporated by reference herein.

FIELD OF THE INVENTION

The present invention relates to a method for continuous production of tablets, including the steps of: providing a rotary tablet press with a plurality of dies, top and bottom punches and a tablet press feeder, providing at least one first material feeder with an inlet and a discharge end, providing at least one second material feeder with an inlet and a discharge end, providing a blender with an inlet end and a discharge end, connecting the inlet of the blender to the discharge ends of the first and second material feeders, connecting the discharge end of the blender to the tablet press feeder, feeding a first material having a first predefined mean particle size to the first material feeder, feeding a second material having a second predefined mean particle size to the second material feeder, mixing the first material with the second material in the blender, feeding the mixed material stream from the discharge end of the blender to the tablet press, and tabletting the mixed material stream in the tablet press. The invention furthermore relates to a tabletting system, and use of the tabletting system for the production of tablets of at least two ingredients containing particles with a significant difference in particle size and/or significant difference in particle size distribution.

BACKGROUND OF THE INVENTION

Over recent years, there has been an increasing interest, in general and in particular within the pharmaceutical industry, to provide products of a larger variety as regards the composition and release profile of the ingredients. In order to produce tablets from for instance active pharmaceutical ingredients (API) and various excipients, the product streams are normally supplied in a powdery form to a tablet press, such as for instance the rotary tablet press described in WO 03/020499 A1 (Courtoy).

One of the later developments of tablets includes the so-called multiple unit tablets. A specific example within this group of tablets is the Multiple-Unit Pellet System tablets, commonly referred to as MUPS®, a registered trademark by AstraZeneca. In multiple unit tablets, the active ingredients are homogeneously distributed in subunits, which can be granules, pellets or even microtablets. By applying specific coatings around the subunits, the release profile of the active ingredient can be controlled or modified. Before the subunits can be compressed into tablets, they are blended with one or more excipients (e.g. fillers, binders, disintegrants etc.). The excipients are required to obtain tablet with desired hardness, friability and disintegration characteristics and fulfil a cushioning role to prevent damage of the pellets during compression.

The production of multiple unit tablets is generally recognized as complicated and challenging. This is in part due to the number of steps involved in the process, viz. pellet manufacture and coating, and the subsequent mixing and blending with excipients, followed by tabletting and coating or other after-treatment of the finished tablets. Furthermore, it is important to ensure that the pellets are not damaged during compression. One other major challenge resides in the fact that during production, the multiple unit tablet feed is particularly prone to segregation due to the broad particle size distribution and/or the significant difference in particle size between the subunits and the excipient(s), respectively. The theory underlying the possible mechanisms of segregation, including percolation and elutriation, is relatively complicated but it is generally recognized that difference in particle size and particle size distribution of the materials involved have a great impact. The average particle size of the pellets typically lies in the range 200-2000 µm, whereas the particle size of the excipient typically lies in the range 100-200 µm. In turn, this entails that during handling and transport from the blender and the intermediate hopper towards the tablet press, there is a risk of segregation of the feed, which is detrimental to the distribution within the feed and which may also entail damage of the pellets due to pellet-to-pellet contact. In addition, the segregation may have a large impact on the content uniformity of the tablets and there is a risk of producing tablets of an inferior quality or at least outside specification if not attended to.

A further issue in the overall production costs is the configuration of the process line. Typically, manufacturing processes hitherto employed within the pharmaceutical field are most often of a batch nature. As an example, WO 02/067854 A2 (King Pharmaceuticals) may be cited. Here, an apparatus for transporting drug formulations from a blender to a tabletting machine is disclosed, wherein a mass flow of material in multiple stages via a portable container is aimed at. Batch manufacturing processes have a number of advantages and provide satisfactory results within many areas. However, due the increasingly widespread application of regulated criteria for monitoring and controlling in particular pharmaceutical manufacturing processes, and to the general increase in the demands to quality by design, the level of quality of monitoring and control attainable by a batch process is often not sufficient, i.a. due to the fact that settings are fixed. Furthermore, a relatively large buffer volume is required, entailing undesired back-mixing of the material stream. As a consequence, manufacturers' and customers' focus of interest has shifted to continuous processes.

In WO 2010/128359 A1 (GEA Pharma Systems), a contained module being able to operate by a fully continuous process for the production of tablets is devised. In such modules and processes, one or more mixing and transportation units are utilised. The term "mixing unit" should in this context be understood in its broadest terms. Thus, the mixing unit refers to a unit operation generally capable of mixing or otherwise processing one, two or more components into a desired form. The mixing unit may thus also be capable of modifying the physical form of dry component(s) processed in the mixing unit, e.g. a feed stream of powder(s) may be converted to a granulate comprising the component (s). The mixing unit may be a granulator for making a granulate from dry powders, such as a granulator to which a granulating liquid is added, or a roller compactor. Further examples include a twin screw blender and a twin screw granulator. Furthermore, the mixing unit may include such equipment as a dryer, a dry blender, a continuous dry blender or the like.

The contained module and the method disclosed in the abovementioned document WO 2010/128359 A1 have proven to function very well with APIs and excipients in powdery form and with a relatively homogenous particle size and particle size distribution, and are particularly efficient in providing improved protection of the operator and the environment by the containment feature. In practical embodiments, the module comprises a number of mixing units in the process line.

However, with respect to the processing/tabletting of at least two product streams having significantly different particle sizes and/or particle size distributions, there is still room for improvement. This applies in particular to tabletting of pharmaceuticals, nutriceuticals, detergents, ceramics, metallic powders and nuclear fuels.

SUMMARY OF THE INVENTION

On this background, it is an object of the present invention to provide a method of the kind mentioned in the introduction, by which the production conditions are improved and by which it is possible to improve the efficiency and reduce the risk of quality deterioration.

In a first aspect, this and further objects are met by a method of the kind mentioned in the introduction, wherein the blender is positioned in close connection with the tablet press, and wherein the mixing step is carried out while transporting the mixed material stream substantially vertically from an upper level to a lower level.

The invention is applicable to all kinds of pharma and non-pharma applications whereby two or more product streams with significantly different particle size and/or significantly different particle size distribution need to be uniformly blended and then compressed.

In another aspect, a tabletting system is provided, comprising a rotary tablet press with a plurality of dies, top and bottom punches and a tablet press feeder, at least one first material feeder with an inlet and a discharge end, at least one second material feeder with an inlet and a discharge end, a blender with an inlet end and a discharge end, the inlet of the blender being connected to the discharge ends of the first and second material feeders, and the discharge end of the blender being connected to the tablet press feeder, the tabletting system being characterized in that the inlet end of the blender is positioned at a level higher than the level of the discharge end in the vertical direction, and that the blender is positioned in close connection with the tablet press.

In this manner, the mixed material stream is transported downwards during the mixing. Without wishing to be bound by theory, it is assumed that this entails that the risk of segregation is diminished to a large extent.

The discharge end of the blender may be connected directly to the tablet press feeder, or via a vertical transition tube, the tablet press feeder being in that case positioned at a level lower than the level of the discharge end in the vertical direction.

In general, the particular advantages of continuous processing are enhanced by the close connection with the tablet press. Among other things, the limited volume of aggregated material in the line entails a better traceability of the material and a limitation of the distance, in which segregation may occur. Preferably, the distance between the discharge end of the blender and the tablet press feeder is below 1 m. In a preferred embodiment, the distance between the discharge end of the blender and the tablet press feeder is below 600 mm.

In a development of the embodiment comprising a vertical transition tube, the vertical transition tube comprises an element promoting plug flow, preferably a plow feeder. Plug flow reduces the risk of segregation that can be induced by preferential flow and differential flow velocities within the stream of mixed material.

In a third aspect of the invention, use of the tabletting system is provided for the production of tablets of at least two ingredients containing particles with a significant difference in particle size and/or significant difference in particle size distribution.

It has turned out that the invention is applicable for the production of tablets of ingredients of which one material has a relatively large mean particle size and the other material a relatively small mean particle size. Ratios of 1.5:1, 2:1 or even larger than 3:1 are foreseen.

Further details and advantages appear from the remaining dependent claims, and from the detailed description of preferred embodiments and examples for carrying out the method set forth below.

DETAILED DESCRIPTION OF THE INVENTION AND OF PREFERRED EMBODIMENTS

Figure 1:
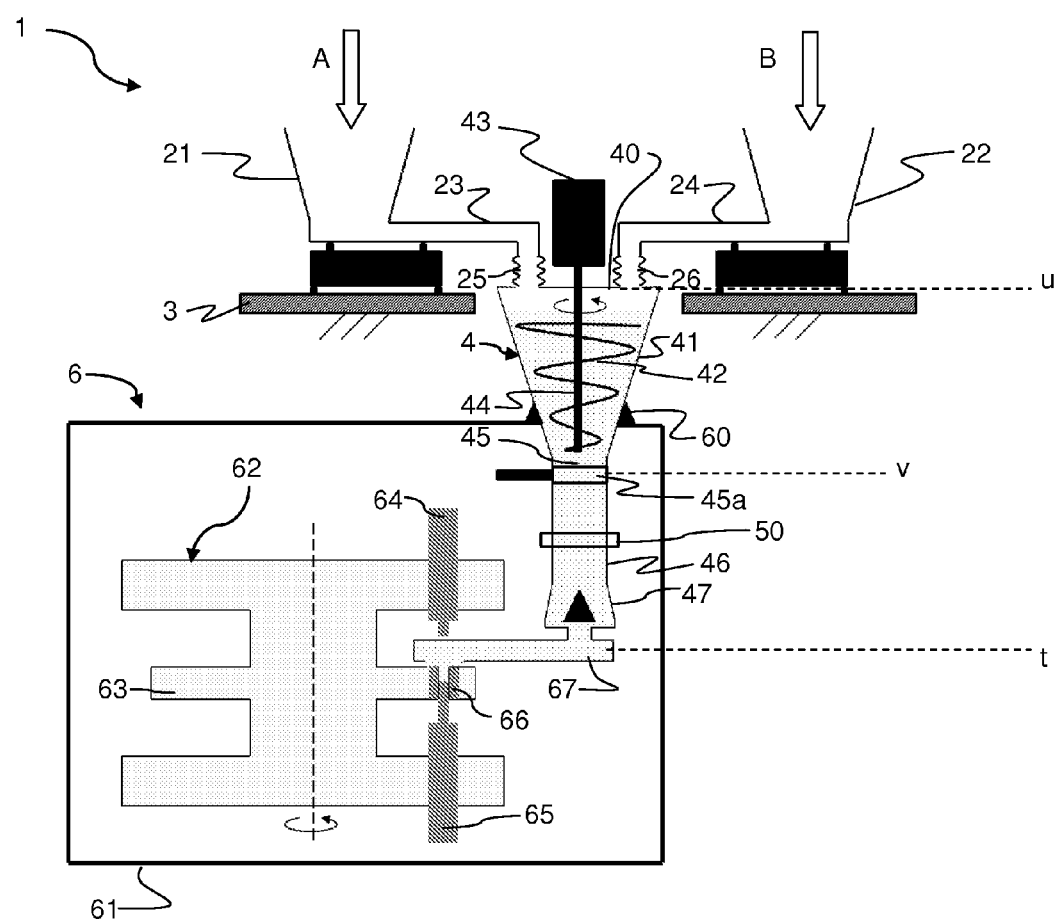
FIG. 1 shows a schematic overview of a tabletting system in an embodiment of the invention.

Referring first to the schematic overview of FIG. 1 showing a first embodiment of a tabletting system generally designated 1, the tabletting system 1 comprises a tablet press 6 of any suitable configuration, for instance a rotary tablet press as described in WO 03/020499 A1. Thus, in a manner known per se the tablet press 6 comprises a housing 61 and a turret 62, in which a die table 63 is present and includes a plurality of dies 66. Top and bottom punches 64, 65 are adapted to reciprocate in the vertical direction to compress the material fed to the dies 66 in the die table 63 during rotation of the turret 62. The material is fed to the dies 66 by means of tablet press feeder 67, which may be a paddle feeder. Other elements may be present in the tablet press and means for controlling the tablet press according to desired settings may be provided.

In order to produce tablets of at least two ingredients containing particles with a significant difference in particle size and/or particle size distribution, special precautions must be taken during feeding and blending/mixing which take place upstream of the tablet press 6 as will be described in detail below. The at least two ingredients may for instance be pellets and excipients, respectively, of multiple unit tablets, but the invention may also be applied in other applications requiring particular measures during the blending/mixing and tabletting. Such tablets typically consist of 30% of pellets and 70% of excipient, but the composition may vary strongly. The excipient can be a single component or a blend of different components, like fillers, binders, disintegrants etc. Furthermore, the excipient also fulfils a cushioning role to prevent damage of the pellets during compression by forming a plastic layer around the pellets.

As shown in FIG. 1, a first material feeder 21 is provided with an inlet for receiving a first material stream A, which in the embodiment shown is constituted by excipient as a pre-blended mix, and a discharge end 23. A second material feeder 22 is provided with an inlet and for receiving a second material stream B, which in the embodiment shown is constituted by pellets, and a discharge end 24. At the respective discharge end 23, 24, each feeder 21, 22 has a connection 25, 26 to an inlet end 40 of a blender 4. The connections 25, 26 may be open or provided as bellows or lay flat tubes made of a lightweight material having a very low stiffness. This is particularly important if the feeders are Loss-In-Weight (LIW) feeders, such that the weighing signal is left almost completely unaffected. The feeders 21, 22 may also take other forms, such as other forms of gravimetric feeders, for instance weight belt feeders, or volumetric feeders such as screw feeders, rotary valves, vibratory feeders, belt feeders or any other suitable kind. Each feeder 21, 22 may for instance be manufactured as individual feeder units as disclosed in Applicant's PCT applications (not yet published), the contents of which are incorporated by reference, and in which each feeder unit comprises a feeder part with a storage hopper to contain material to be processed, and a weighing cell. Furthermore, each such feeder includes a conveyer leading to a discharge end, the conveyer having the function of transporting the material from the storage hopper to discharge the material into a suitable receiving container. Refilling of the storage hoppers may take place intermittently at different points in time, if expedient according to a predefined schedule.

The blender 4 with its inlet end 40 is positioned at a level u which in the embodiment shown is slightly below the discharge ends 23, 24 of the first and second material feeders 21, 22, but which may also be substantially level therewith or substantially above the blender 4. Downwards as seen in the vertical direction, the blender 4 is provided with a discharge end 45 at a level v below level u. The inlet 40 of the blender 4 is thus connected to the discharge ends 23, 24 of the first and second material feeders 21, 22, and the discharge end 45 of the blender 4 is connected to the tablet press feeder 67 such that the inlet end 40 of the blender 4 is positioned at a level u higher than the level v of the discharge end 45. The distance between levels u and v corresponds to the height of the blender 4 and is typically 150 to 600 mm. Through the passage in the blender 4, the material streams A and B are mixed to form a mixed material stream which in addition to being mixed is transported downwards. That is, blending and vertical transport are combined, thus reducing the vertical distance over which segregation of pellets and excipient can occur. Further, the blender inlet is positioned vertically above the blender discharge end, maximizing the vertical distance bridged by the blender and at the same time minimizing the footprint of the blender. The blender 4 is positioned closely to the tablet press 6, namely in the embodiment shown just above the tablet press 6. Furthermore, in the embodiment shown, the first material feeder 21 and the second material feeder 22 are positioned in close connection to the blender 4 However, this is no requirement to the functioning of the invention.

In principle, the discharge end of the blender could be connected directly to the tablet press feeder. However, in the embodiment shown, the discharge end 45 of the blender 4 is connected to the tablet press feeder 67 via a vertical transition tube 46, the tablet press feeder 67 being positioned at a level t lower than the level v of the discharge end 45. The distance between level t and level v substantially corresponds to the length of the transition tube 46 and is normally aimed at keeping as low as possible. Preferably, the distance is below 1 m, more preferred below 600 mm. A suitable range of the distance may for instance lie in the range 200 to 600 mm.

As shown, the inlet end 40 and discharge end 45 are substantially concentric, i.e. are substantially aligned in the vertical direction. This entails a particularly compact footprint, reduces the area occupied by the tabletting system and decreases or eliminates the problem of product segregation upstream of the tablet press feeder 67.

In the embodiment shown, the blender 4 is a ribbon blender, namely a conical ribbon blender having a conical housing 41 in which a spiral 42 is rotated by means of a driving unit comprising a motor 43 driving a shaft 44. The ribbon blender does not require a free fall of powder at the outlet of the blender, hence further reducing the risk of segregation (during free fall, small/lighter particles are more easily entrained by air, and will settle more slowly than larger/heavier particles).

However, other vertical blenders or mixers are conceivable, whereby the inlet and outlet are substantially in line with each other and have a vertical product stream.

Figure 2:
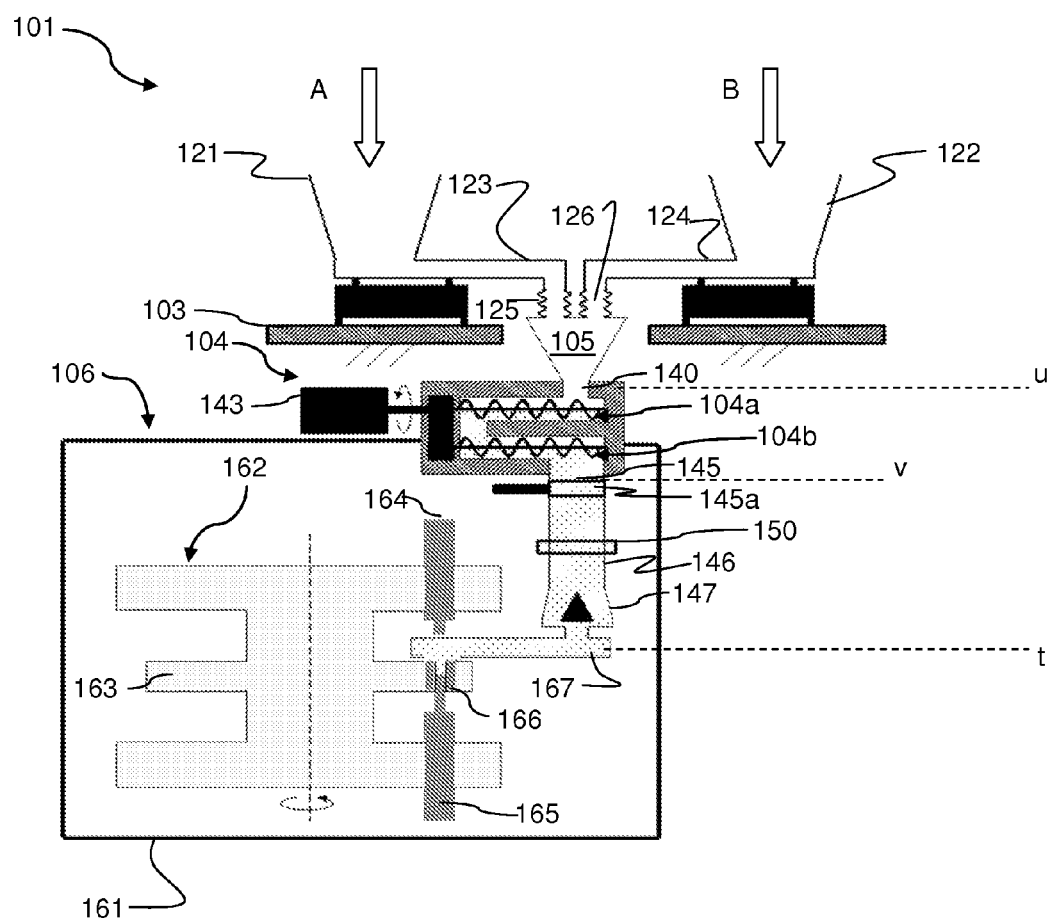
FIG. 2 shows a schematic overview of a tabletting system in an alternative embodiment of the invention.

In an alternative embodiment, shown in FIG. 2, elements having the same or analogous function as in the first embodiment of FIG. 1 carry the same reference numerals to which 100 has been added. Only differences relative to the first embodiment will be described in detail. The blender 104 comprises a first screw blender 104a and a second screw blender 104b spanning a certain vertical distance between the inlet end 140 and the discharge end 145. In this embodiment, it is possible to operate the first and second screw blenders 104a, 104b at different rotational speed values and possibly also in counter-rotation. From the discharge ends 124, 126 from the first and second material feeders 121, 122, the two material streams A and B are discharged into a common receiving container 105 such as a hopper being in direct connection with the blender 104.

Returning to the embodiment shown in FIG. 1, the discharge end 45 of the blender 4 comprises a shut-off valve 45a. This shut-off valve can be a butterfly valve, ball valve, pinch valve, gate valve, diaphragm valve, or any other suitable kind.

Furthermore, the vertical transition tube 46 comprises a plow feeder generally designated 47. This plow feeder consists of a horizontal bottom plate with a central discharge opening connected to the press feeder 67, an internal cone centrally positioned at a given distance above this discharge opening, and one or more discharge arms which are positioned between the cone and discharge opening and connected to a drive. When the feeder drive is not engaged, the natural angle of repose prevents material from flowing down the discharge opening. Upon engagement of the drive, the discharge arms rotate around the central vertical axis and actively move the material from the complete cross-section of the feeder into the central discharge opening. In combination with a suitable design, the use of this plow feeder avoids preferential powder flow and differential flow velocities in the vertical transition tube 46, and reduces the associated risk of segregation. Alternatively, also other elements that ensure plug flow in either passive or active way could be comprised into the vertical transition tube 46. All in all, feeding of the mixed material stream in plug flow is aimed at and obtained, thus avoiding segregation of the blend.

In the embodiment shown, a PAT sensor 50 is provided in the transition tube 46 above the tablet press feeder 67 to verify the uniformity of the blend. This can be a NIR sensor, Raman sensor, camera etc. Other PAT sensors may be provided at other positions in the tabletting system 1.

Although not shown, the tabletting system 1 may furthermore comprise a level sensor in the blender sensing the level of material inside the blender 4. This allows synchronization of the speed of the tablet press and the speed of the feeders.

Level sensing inside the blender can be continuous or be based on several level sensors at certain critical positions (digital pulses).

Figure 3A:
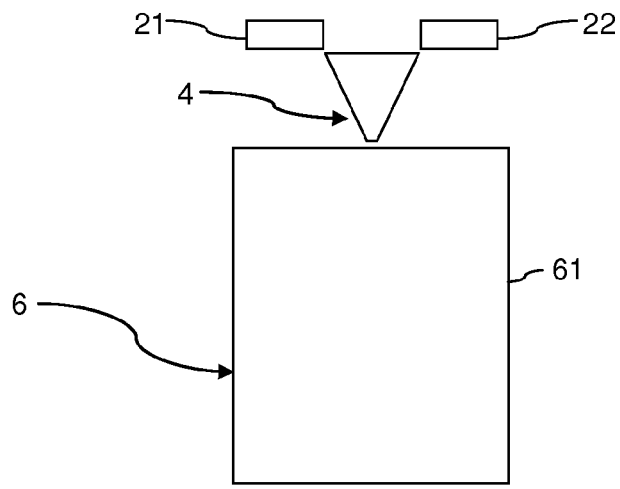
FIGS. 3a to 3c show schematic drawings of conceivable configurations of a tabletting system in embodiments of the invention.
Figure 3B:
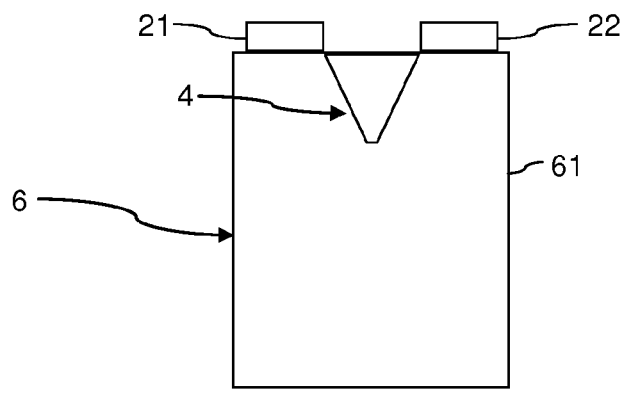
Figure 3C:
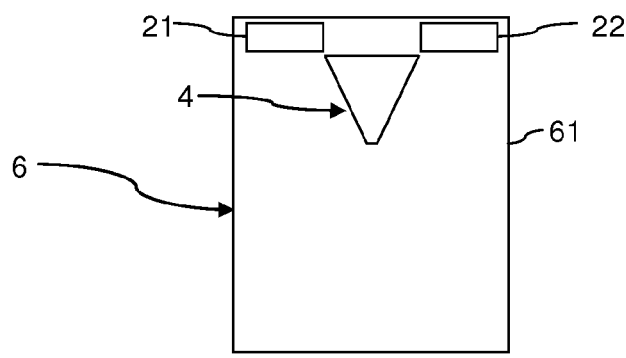

Referring now to FIGS. 3a to 3c, three different configurations of the material feeders 21, 22 and the blender 4 relative to the housing 61 of the tablet press 6 are shown.

In the embodiment of FIG. 1, the first and second material feeders 21, 22 are located on a separate support plate 3. This corresponds in substance to the configuration of FIG. 3a, in which the feeders 21, 22 are positioned outside and on a higher level than the housing 61 of the tablet press 6, the blender 4 being positioned partly (FIG. 1) or wholly (FIG. 3a) outside the housing 61 of the tablet press 6. In the actual embodiment of FIG. 1, the blender 4 is supported by support structure 60 of the housing 61 of the tablet press 6. As a further alternative (not-shown), the blender may be positioned inside the housing of the press and the feeders outside on a separate support.

Alternatively, the first and second material feeders 21, 22 are mounted on the tablet press 6, the blender 4 being positioned partly (not shown) or wholly (FIG. 3b) inside the housing 61 of the tablet press 6.

As a further alternative, the first and second material feeders 21, 22, and the blender 4 are positioned wholly inside the housing 61 of the tablet press 6 as shown in FIG. 3c.

Operation of the tabletting system 1 is advantageously carried out by the inventive method for continuous production of tablets, including the steps of:
provide a tablet press with a plurality of dies, top and bottom punches and a tablet press feeder,
providing at least one first material feeder with an inlet and a discharge end,
providing at least one second material feeder with an inlet and a discharge end,
providing a blender with an inlet end and a discharge end,
connecting the inlet of the blender to the discharge ends of the first and second material feeders,
connecting the discharge end of the blender to the tablet press feeder,
feeding a first material having a first predefined mean particle size to the first material feeder,
feeding a second material having a second predefined mean particle size to the second material feeder,
mixing the first material with the second material in the blender,
feeding the mixed material stream from the discharge end of the blender to the tablet press, and
tabletting the mixed material stream in the tablet press,
wherein the blender is positioned in close connection with the tablet press, and
wherein the mixing step is carried out while transporting the mixed material stream substantially vertically from an upper level to a lower level.

Use of the tabletting system 1 is foreseen for the production of tablets of at least two ingredients containing particles with a significant difference in particle size. This is particularly advantageous in the production of for instance multiple unit tablets or other compositions in which the mean particle size of the pellets is more than 200 μm and the mean particle size of the excipient is less than 200 μm. In other tablets, the mean particle size of the one material may be more than 300 μm and the mean particle size of the excipient is less than 200 μm. Even a mean particle size of more than 500 μm of one material/pellets, and a mean particle size of the other material/excipient is less than 200 μm.

The invention should not be regarded as being limited to the embodiments shown and described in the above. Several modifications and combinations are conceivable within the scope of the appended claims.

The invention claimed is:

1. A method for continuous production of tablets, the method comprising:
providing a rotary tablet press with a plurality of dies, a top punch, a bottom punch, and a tablet press feeder;
providing at least one first material feeder with an inlet and a discharge end;
providing at least one second material feeder with an inlet and a discharge end;
providing a blender with an inlet end and a discharge end, wherein the blender is positioned in close connection with the rotary tablet press;
connecting the inlet of the blender to the discharge ends of the first and second material feeders;
connecting the discharge end of the blender to the tablet press feeder;
feeding a first material having a first predefined mean particle size to the first material feeder;
feeding a second material containing particles having a second pre-defined mean particle size significantly different from the first material to the second material feeder;
mixing the first material with the second material in the blender into a mixed material stream while transporting the mixed material stream substantially vertically from an upper level to a lower level;
feeding the mixed material stream from the discharge end of the blender to the rotary tablet press; and
tabletting the mixed material stream in the rotary tablet press.

2. The method of claim 1, wherein multiple unit tablets are produced from pellets and excipient as the first and second material.

3. The method of claim 1, wherein the mean particle size of one of the first or second material is more than 200 μm and the mean particle size of the other of the first or second material is less than 200 μm.

4. The method of claim 3, wherein the mean particle size of one of the first or second material is more than 300 μm.

5. The method of claim 4, wherein the mean particle size of one of the first or second material is more than 500 μm.

6. The method of claim 1, wherein a ratio of the mean particle size of one of the first or second material and the mean particle size of the other of the first or second material is larger than 1.5:1.

7. The method of claim 1, wherein the mixed material stream is fed to the tablet press feeder of the rotary tablet press in plug flow.

8. A system comprising:
a rotary tablet press comprising a plurality of dies, a top punch, a bottom punch, and a tablet press feeder;
at least one first material feeder with an inlet and a discharge end;
at least one second material feeder with an inlet and a discharge end; and
a blender with an inlet end and a discharge end, the inlet of the blender being connected to the discharge ends of the first and second material feeders, and the discharge end of the blender being connected to the tablet press feeder via a vertical transition tube, the tablet press feeder being positioned at a level lower than the level of the discharge end of the blender in a vertical direction and wherein the vertical transition tube comprises a plow feeder configured to promote plug flow, and wherein the inlet end of the blender is positioned at a level higher than the level of the discharge end of the blender in the vertical direction, and that the blender is positioned in close connection with the rotary tablet press.

9. The system according to claim 8, wherein the distance between the discharge end of the blender and the tablet press feeder is less than 1 meter.

10. The system according to claim 8, wherein the inlet end and the discharge end of the blender are substantially aligned in the vertical direction.

11. The system according to claim 8, wherein the blender is a ribbon blender.

12. The system according to claim 8, wherein the blender comprises a first screw blender and a second screw blender spanning a given vertical distance between the inlet end and the discharge end of the blender.

13. The system according to claim 8, wherein the first and second material feeders are Loss-in-Weight (LIW) feeders.

14. The system according to claim 8, wherein the discharge end of the blender comprises a shut-off valve.

15. The system according to claim 8, further comprising at least one PAT sensor is provided.

16. The system according to claim 8, wherein the first and second material feeders are mounted on at least one of:

a separate support plate outside of and on a higher level than the rotary tablet press; or a housing of the rotary tablet press or on a separate support outside the housing.

17. The system according to claim 16, wherein the blender is positioned at least partially inside the housing of the rotary tablet press.

18. A system comprising:

a rotary tablet press comprising a plurality of dies, a top punch, a bottom punch, and a tablet press feeder;

at least one first material feeder with an inlet and a discharge end;

at least one second material feeder with an inlet and a discharge end; and a blender with an inlet end and a discharge end, the inlet of the blender being connected to the discharge ends of the first and second material feeders, and the discharge end of the blender being connected to the tablet press feeder, wherein the inlet end of the blender is positioned at a level higher than the level of the discharge end of the blender in a vertical direction, and that the blender is positioned in close connection with the rotary tablet press, and wherein the blender comprises a first screw blender and a second screw blender spanning a given vertical distance between the inlet end and the discharge end of the blender.

* * * * *